(12) United States Patent
Sherman

(10) Patent No.: US 6,894,066 B2
(45) Date of Patent: *May 17, 2005

US006894066B2

(54) MAGNESIUM SALT OF S-OMEPRAZOLE

(75) Inventor: Bernard Charles Sherman, 50 Old Colony Road, Toronto, Ontario (CA), M2L 2K1

(73) Assignee: Bernard Charles Sherman, Ontario (CA)

(*) Notice: Subject to any disclaimer, the term of this patent is extended or adjusted under 35 U.S.C. 154(b) by 0 days.

This patent is subject to a terminal disclaimer.

(21) Appl. No.: 10/439,233

(22) Filed: May 16, 2003

(65) Prior Publication Data

US 2003/0232861 A1 Dec. 18, 2003

Related U.S. Application Data

(63) Continuation-in-part of application No. 10/129,622, filed on May 9, 2002, now Pat. No. 6,713,495.

(30) Foreign Application Priority Data

May 17, 2002 (CA) ............................................. 2386716

(51) Int. Cl.⁷ .................. A61K 31/4439; C07D 401/12
(52) U.S. Cl. ..................................... 514/338; 546/273.7
(58) Field of Search ........................ 514/338; 546/273.7

(56) References Cited

U.S. PATENT DOCUMENTS

5,714,504 A * 2/1998 Lindberg et al. ............ 514/338
6,048,981 A * 4/2000 Macel ...................... 546/273.4
6,713,495 B1 * 3/2004 Sherman ..................... 514/338

FOREIGN PATENT DOCUMENTS

WO 01/87831 * 11/2001

OTHER PUBLICATIONS

Chemical & Engineering News, Feb. 2003, pps 32–35.*
US Pharmacopia, 1995, pp. 1843–1844.*
Halbein et al., J. of Pharm. Sci., 58 (1969) pp 911–928.*
Concise Enclyclopedia Chemistry, pp. 872–873 (1993).*

* cited by examiner

*Primary Examiner*—Patricia L. Morris
(74) *Attorney, Agent, or Firm*—Neil H. Hughes; Ivor M. Hughes; Marcello Sarkis

(57) ABSTRACT

A process of producing the magnesium salt of an enantiomer of omeprazole, said process comprising the steps of:
  i) reacting magnesium with a lower alcohol to produce magnesium alkoxide in solution in the lower alcohol as solvent,
  ii) adding the neutral form of the enantiomer of omeprazole to the solution, and
  iii) flash-evaporating the solvent.

28 Claims, No Drawings

MAGNESIUM SALT OF S-OMEPRAZOLE

This Application is a Continuation-In-Part Application of U.S. application Ser. No. 10/129,622 filed May 9, 2002 now U.S. Pat. No. 6,713,495 the contents of which the application is incorporated herein by reference.

TITLE OF INVENTION

MAGNESIUM SALT OF S-OMEPRAZOLE

FIELD OF THE INVENTION

The present invention relates to an improved form of the magnesium salt of S-omeprazole, a process for making same, and pharmaceutical compositions thereof.

BACKGROUND OF THE INVENTION

The compound known under the generic name omeprazole is described in European patent 0005129. Further, European Patent No. 124,495 describes the advantages of providing the salts of omeprazole and particularly the magnesium salt thereof.

Omeprazole is useful for inhibiting gastric acid secretion and has gastric mucosa protective activity in mammals and man. Omeprazole may be used for prevention and treatment of gastric acid related disorders and gastrointestinal inflammatory diseases in mammals and man, including for example gastritis, gastric ulcer and duodenal ulcer.

The terms "omeprazole, S-omeprazole and R-omeprazole" as used in this specification designate the neutral form thereof, that is the form without a salt-forming cation present, unless otherwise indicated.

European Patent No. 0124495, in example 5 specifically discloses the synthesis of magnesium omeprazole dihydrate, and example 6 specifically discloses the synthesis of magnesium omeprazole anhydrate. Manufacturing of the described magnesium omeprazole salt presents significant difficulties.

The process of manufacture and isolation of the dihydrate according to example 5 is relatively complex. It requires making the sodium salt, adding a solution of magnesium chloride to obtain a precipitate, removing water by centrifuging the precipitate, washing the precipitate with deionized water until no Cl⁻ is detectable, drying in air, grinding, and then drying in vacuum at 40° C. for 24h. Moreover, because the resulting magnesium omeprazole dihydrate is crystalline, the rate of dissolution in intestinal fluid is relatively slow, unless the material is milled to a relatively fine particle size. It would therefore be desirable to provide non-crystalline forms to improve the dissolution in intestinal fluid.

The process of making the anhydrate according to example 6 is simpler. Magnesium is reacted with methanol to give a solution of magnesium methoxide in methanol. The solution is added to a solution of omeprazole in methanol, the quantity of omeprazole being one mole for each two moles of magnesium. The methanol is then evaporated to give a crystalline solid, which is magnesium omeprazole anhydrate. However, the anhydrate as made by this process is also not without a problem. As the magnesium omeprazole precipitates from the solution upon evaporation of the methanol, residual methanol is entrapped in the solid particles and cannot easily be removed by evaporation. Methanol is toxic and high levels are generally considered unacceptable in pharmaceutical chemicals.

Canadian patent 2166794 describes what is said to be an improved form of magnesium omeprazole dihydrate, which has a higher degree of crystallinity than that of example 5 of EP 0124495. This form has a methanol content of less than 0.1%. However, like the product of example 6 of EP 0124495, it is a crystalline dihydrate, and the process of manufacture is relatively complex.

According to Canadian patent 2166794, the degree of crystallinity of a sample made according to example 6 of EP 0124495 was 67%, whereas the degree of crystallinity of the improved form is at least 70%.

Canadian patent application No. 2254572 discloses improved processes for the production of magnesium omeprazole crystalline dihydrate. The disclosure reviews the prior art, and in particular, in relation to the anhydrate of example 6 of EP 0124495, states as follows: "This procedure cannot be practiced on a large scale because of the need to evaporate to dryness. It has been found that unacceptable and potentially dangerous amounts of methanol become trapped in this solid, making it pharmaceutically unacceptable." The processes of Canadian patent 2254572 are again relatively complex.

Improved processes for the production of magnesium omeprazole crystalline dihydrate are also described in PCT Publication No. WO 97/41114. The degree of crystallinity of the product of example 1 is said to be 80%. Again, the processes disclosed are relatively complex.

Omeprazole is a sulfoxide and a chiral compound, wherein the sulfur atom is the stereogenic center. Thus, omeprazole is a racemic mixture of its two single enantiomers, the R and S-enantiomer of omeprazole, herein referred to as R-omeprazole and S-omeprazole. The absolute configurations of the enantiomers of omeprazole have been determined by an X-ray study of an N-alkylated derivative of the (+)-enantiomer in non-salt form. The (+)-enantiomer of the non-salt form and the (−)-enantiomer of the non-salt form were found to have R and S configuration, respectively, and the (+)-enantiomer of the magnesium salt and the (−)-enantiomer of the magnesium salt were also found to have R and S configuration, respectively. The conditions for the optical rotation measurement for each of these enantiomers are described in WO 94/27988.

Certain salts of single enantiomers of omeprazole and their preparation are disclosed in WO 94/27988. These compounds have improved pharmacokinetic and metabolic properties which will give an improved therapeutic profile such as a lower degree of interindividual variation.

WO 96/02535 discloses a process for the preparation of the single enantiomers of omeprazole and salts thereof, and WO 96/01623 discloses a suitable tableted dosage form for instance magnesium salts of R- and S-omeprazole. The magnesium salt of S-omeprazole trihydrate described is substantially free from magnesium salts of R-omeprazole.

U.S. Pat. No. 5,714,504 describes optically pure salts of omeprazole and in particular the sodium and magnesium salts thereof as pure crystalline enantiomeric salts, and in one embodiment optically pure crystalline magnesium salts. The patent describes the non-aqueous process for the preparation of crystalline forms of the magnesium salts of optically pure enantiomers of omeprazole or analogues thereof; which include the steps of stirring a crude preparation of the omeprazole enantiomer under nitrogen into a methanolic magnesium methoxide solution, precipitating inorganic magnesium salts with the addition of a small amount of water, removing any precipitated inorganic magnesium salts, concentrating the residual methanolic solution, precipitating the omeprazole enantiomer by adding acetone to the residual solution, and filtering off the optically pure enantiomer crystals of magnesium omeprazole or analogues thereof. Because it is possible to purify optically impure or partially pure salts of the enantiomers of omeprazole by crystallization, they can be obtained in very high optically pure, namely greater than or equal to 99.8% enantiomeric excess. Example 6 within the specification describes the preparation of the magnesium salt of S-omeprazole by crystallization of said salt.

The preferred enantiomer of omeprazole referred to as the (−)-enantiomer of omeprazole or a pharmaceutical salt thereof, is said to be an improved alternative to omeprazole in the treatment of gastric acid related diseases which provides higher dose efficiencies and less inter-individual variation in plasma levels, both between rapid and slow metabolizers and within the group of rapid metabolizers, as taught in U.S. Pat. No. 5,877,192. The major emphasis described relates to various forms of the enantiomers of omeprazole and salts thereof in crystalline form and preferably in highly crystalline form, which are also described in Canadian Patent Application No. 2,357,744. Although amorphous forms are nominally discussed there is no specific teaching as to the advantages of preventing crystals from forming. Therefore, a need exists for the magnesium salts of enantiomers of omeprazole having a desirable low methanol content.

U.S. Pat. No. 6,262,085 teaches in example 20 the magnesium salt of S-omeprazole. Generally, the patent describes the preferred crystalline form but states that other forms such as amorphous forms are casually mentioned, but clearly the teaching refers to crystalline and particularly to the co-crystalline form wherein enantiomers of omeprazole are present in the same crystal lattice and co-crystallized from solution. However, there is no teaching as to the manner in which amorphous forms in particular might be prepared, resulting in the same deficiencies with reference to solvent content as described above.

It would therefore be highly desirable to provide primarily amorphous magnesium salt of the enantimers of omeprazole and particularly the magnesium salt of S-omeprazole, since these salts have surprisingly high stability in alkaline conditions. There still exists a need for magnesium salts of enantiomers of omeprazole having substantially low methanol content and having a minimum amount of crystallinity with a large percentage of the material being amorphous, that is having minimum crystalline structure.

In summary, the only magnesium omeprazole according to the prior art that has an acceptably low level of methanol is magnesium omeprazole crystalline dihydrate, which has a degree of crystallinity of 67% or higher and is produced only by relatively complex processes.

In light of the foregoing, the object of the present invention is to produce magnesium omeprazole and the magnesium salt of enantiomers of omeprazole having acceptably low levels of methanol, but containing a large proportion of amorphous material (non-crystalline), which preferably may also be substantially amorphous as well, to be produced by a simple process.

It is also an object of this invention to provide the magnesium salt of S-omeprazole in pharmaceutically acceptable forms.

It is a further object of the invention to provide the magnesium salt of R-omeprazole in pharmaceutically acceptable forms.

Further and other objects of the invention will become apparent to those skilled in the art when considering the following summary of the invention and the more detailed description of the preferred embodiments and examples contained herein.

BRIEF SUMMARY OF THE INVENTION

According to one aspect of the invention magnesium omeprazole of the present invention is made by reacting magnesium in a lower alcohol to form magnesium alkoxide, preferably adding omeprazole in a quantity of about two moles per mole of magnesium, and flash-evaporating the alcohol, so as to form a solid precipitate without allowing the growth of crystals or particles that entrap the alcohol at unacceptable levels. The resulting material is substantially amorphous (non-crystalline).

According to a primary aspect of the invention the magnesium salt of the enantiomers of omeprazole of the present invention is made by reacting magnesium in a lower alcohol to form magnesium alkoxide, adding only one of the enantiomers of omeprazole in neutral form, for example S-omeprazole, or alternatively R-omeprazole, preferably in a quantity of about 2 moles per mole of magnesium, and flash evaporating the alcohol, so as to form a solid precipitate without allowing the substantial growth of crystals or particles that entrap the alcohol at unacceptable levels. The resulting material contains a desirable level of non-crystalline material, and preferably a primarily amorphous amount of the magnesium salts of either of the enantiomers of omeprazole, and preferably magnesium S-omeprazole. In another embodiment a substantially amorphous form is provided.

According to yet another aspect of the invention there is provided a process of producing the magnesium salt of an enantiomer of omeprazole, said process comprising the steps of:
  i) reacting magnesium with a lower alcohol to produce magnesium alkoxide in solution in the lower alcohol as solvent,
  ii) adding the neutral form of the enantiomer of omeprazole to the solution, and
  iii) flash-evaporating the solvent.

In one embodiment the enantiomer is S-omeprazole. In another embodiment the enantiomer is R-omeprazole. Preferably the lower alcohol is methanol.

In one embodiment the flash-evaporation is done by spray-drying the solution.

According to yet another aspect of the invention there is provided magnesium S-omeprazole or alternatively magnesium R-omeprazole having a residual organic solvent content of less than 7% by weight.

According to yet another aspect of the invention there is provided magnesium S-omeprazole or alternatively magnesium R-omeprazole having a degree of crystallinity of under 67% and in one embodiment having a residual organic solvent content of less than 7% by weight, preferably a residual organic solvent content of less than 5% by weight, more preferably a residual organic solvent content of less than 2% by weight, and most preferably a residual organic solvent content of less than 1% by weight.

In one embodiment magnesium S-omeprazole or alternatively magnesium R-omeprazole has a degree of crystallinity of under 60%, preferably has a degree of crystallinity of under 50%, more preferably has a degree of crystallinity of under 25%.

Preferably a solid pharmaceutical composition for oral administration may further comprise magnesium S-omeprazole or alternatively magnesium R-omeprazole as described above, preferably in the form of a tablet, wherein the tablet may be enteric coated. In one embodiment the enteric coated tablet may further comprise a separating layer between said enteric coating and said tablet.

The resulting composition comprising magnesium S-omeprazole or alternatively magnesium R-omeprazole is preferably in substantially amorphous form.

DETAILED DESCRIPTION OF THE INVENTION

In the process of manufacture of magnesium omeprazole, or the magnesium salt of s-omeprazole according to one aspect of the present invention, magnesium is reacted in a lower alcohol, preferably methanol, to form a solution of magnesium alkoxide in the alcohol.

The atomic weight of magnesium is 24.3 and the molecular weight of omeprazole or the neutral form of s-omeprazole is 345.4. Since magnesium is divalent, the amount of magnesium required to convert 345.4 grams of omeprazole or S-omeprazole to magnesium omeprazole or the magnesium salt of s-omeprazole is 12.15 grams.

Hence 35.2 grams of magnesium is needed to convert 1 kilo of omeprazole or the neutral form of s-omeprazole to magnesium omeprazole or magnesium s-omeprazole.

The process of converting 1 kilo of omeprazole or the neutral form of s-omeprazole to magnesium omeprazole or the magnesium salt of s-omeprazole, thus begins with reacting 35.2 grams of magnesium in a lower alcohol, preferably methanol. The minimum amount of methanol needed to react fully and dissolve 35.2 grams of magnesium is about 1000 grams.

When the magnesium is immersed in the alcohol, the reaction will be evident from the generation of hydrogen bubbles, and the reaction will be complete when all the magnesium has been consumed and the effervescence has ceased. All of the magnesium will then be present as magnesium alkoxide in the alcohol (i.e. magnesium methoxide in methanol, if methanol is used as the alcohol).

The omeprazole or the neutral form of s-omeprazole can then be added directly to the magnesium alkoxide solution. Alternatively, the omeprazole or the s-omeprazole (neutral form) may first be dissolved in an alcohol or another organic solvent that is miscible with the alcohol used to make the magnesium alkoxide, and the resultant solution may then be added to the magnesium alkoxide solution.

Where methanol is used as the sole solvent, a total of only about 1.5 kilos is needed for converting 1 kilo of omeprazole or the neutral form of s-omeprazole to magnesium omeprazole or the magnesium salt of S-omeprazole.

Hence, using quantities based on 1 kilo of omeprazole or S-omeprazole (or alternatively R-omeprazole), the simplest and best procedure is to react 35.2 grams of magnesium in about 1.5 kilos of methanol, wait until the magnesium has been fully reacted, and then adding 1 kilo of omeprazole or S-omeprazole to the solution and stir to dissolve. The result will be a solution of magnesium omeprazole or S-omeprazole equivalent to 1 kilo of omeprazole in methanol.

In order to obtain solid, magnesium omeprazole or magnesium S-omeprazole that is substantially free of organic solvent (i.e. substantially free of methanol, if methanol is used), it is then necessary to eliminate the solvent.

It has been found that this can be done according to one aspect of the invention by "flash-evaporating" the solvent. Flash-evaporating will be understood to mean evaporating in such a way as to avoid the precipitation of crystals or large particles which entrap the alcohol.

One method of flash-evaporating the solvent is to mix the solution into a solid excipient such as, for example, microcrystalline cellulose or the like, or any other well known appropriate excipient, so that a damp mass is formed. The mass can then be dried in a conventional oven, a fluid bed drier, or under vacuum to remove the solvent. Because the solution has been dispersed throughout the solid excipient, as the solvent evaporates, the magnesium omeprazole or the magnesium salt of S-omeprazole, is deposited as a thin layer over the surface of the particles of the solid excipient and does not precipitate as crystals or large granules, so that there is little or no entrapment of solvent.

The preferred way of flash-evaporating the solvent is by spray-drying the solution.

It has been found in utilizing the above-mentioned preferred processes that magnesium omeprazole and the magnesium salt of S-omeprazole can be made having a residual solvent content substantially lower than can be achieved by simply evaporating the solvent from the solution under vacuum.

The residual organic solvent content by weight of the magnesium omeprazole, and the magnesium salt of S-omeprazole made according to the present invention will be under 7%, preferably under 5%, more preferably under 2%, and most preferably under 1%.

The degree of crystallinity of the obtained product can be measured with powder X-ray diffraction (XRD) as described in WO 97/41114 as follows: A thin layer of the triturated sample is smeared onto a cut silicon single crystal zero background holder which is rotated during the measurement. Cu K∀ radiation and constant or automatic antiscatter and divergence slits are used to obtain a diffractogram with 2θ from 1 or 2° to at least 35°.

The degree of crystallinity is calculated with the formula:

Degree of crystallinity=100∗$C/(A+C)$ $C$=the area from the peaks in the diffractogram ("the crystalline area"), $A$=the area between the peaks and the background ("the amorphous area").

Area calculations are performed for 2θ between 4–33°. The lowest intensity value found in this interval is chosen as the constant background and subtracted from the area A. When constant slits are used, the increased background at low angles due to the influence from the primary beam is also subtracted from the area A.

The degree of crystallinity of magnesium omeprazole and the magnesium salt of S-omeprazole according to the present invention is under 67%, as compared to 67% or higher for magnesium omeprazole crystalline dihydrate according to the prior art.

The degree of crystallinity will preferably be under 60%, more preferably under 50%, and most preferably under 25%.

If the magnesium omeprazole or the magnesium salt of S-omeprazole of the present invention is made in an environment and using excipients (including the air or other gas used for drying in the spray-dry process) that is completely free of water, the magnesium omeprazole or the magnesium S-omeprazole will be anhydrous. However, pure anhydrous magnesium omeprazole or magnesium S-omeprazole is hygroscopic and it will readily absorb water from air until it reaches an equilibrium water content of about 5% to 8%, depending on the relative humidity of the air. This is not problematic, as it does not adversely affect stability of the final product.

The present invention will be further processed into pharmaceutical compositions such as, for example, tablets for oral administration. The tablets will preferably be enteric coated to protect the magnesium omeprazole and magnesium S-omeprazole from the effects of gastric acid.

The invention will be further understood from the following examples, which are intended to be illustrative and not limiting of the invention.

EXAMPLE 1

1.76 g of pure magnesium was added to 800 g of methanol in a 1000 mL glass flask. The flask was closed with a loose-fitting stopper (loose to allow hydrogen gas to escape), and the flask was allowed to sit overnight.

The next morning it was observed that the magnesium had all been consumed and that the effervescence had ceased, resulting in a slightly hazy solution of magnesium methoxide in methanol. 50 grams of omeprazole (or the neutral form of S-omeprazole could be used) was then added to the contents of the flask and the contents were stirred for several minutes until dissolved to form a solution of magnesium omeprazole (or if the neutral form of S-omeprazole was used, magnesium S-omeprazole) in methanol.

EXAMPLE 2

To produce a reference sample of magnesium omeprazole anhydrate according to the prior art (i.e. example 6 of EP 0124495), about 20% of the solution from step 2 was transferred to a 1000 mL beaker. The beaker was then placed in a vacuum oven for drying under vacuum at 50° C. for a period of 4 hours. At the end of this time, a solid material remained that had no evident odour of residual methanol. This solid material was tested to determine the level of residual methanol, which was found to be 7.2% by weight.

EXAMPLE 3

To produce the present invention, the balance of the solution of Example 1 was spray-dried on a Yamato® spray-dryer, using an inlet air temperature of about 140° C. and outlet air temperature of about 70° C.

The resulting dry material was a fine powder, which appeared non-crystalline (i.e. amorphous) and also had no evident odour of residual methanol. The powder was tested to determine the level of residual methanol, which was found to be 0.7%.

This powder was examined for crystallinity by powder X-ray diffraction, and it was found that the powder was primarily amorphous (non-crystalline), having a degree of crystallinity of under 25%.

EXAMPLE 4

The following ingredients are to be mixed together in the proportions shown:

| | |
|---|---|
| Magnesium S-omeprazole (prepared according to Examples 1 and 3) | 21.0 |
| Anhydrous lactose | 131.0 |
| Croscarmellose sodium | 6.4 |
| Magnesium stearate | 1.6 |
| | 160.0 |

The mixture is to be compressed into tablets having a weight of 160 mg per tablet, so that each tablet will contain 21 mg of magnesium S-omeprazole, which is equivalent to about 20 mg of omeprazole.

A sub-coating comprising hydroxypropyl methylcellulose dissolved in water will then be applied to the tablets by spray-application in a side-vented coating pan.

An enteric coating is to be applied over the sub-coating by spray-application of methacrylic acid copolymer aqueous dispersion, with triethyl citrate dissolved therein as plasticizer.

As many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. A process of producing the magnesium salt of an enantiomer of omeprazole, said process comprising the steps of:
   i) reacting magnesium with a lower alcohol to produce magnesium alkoxide in solution in the lower alcohol as solvent,
   ii) adding the neutral form of the enantiomer of omeprazole to the solution, and
   iii) flash-evaporating the solvent yielding an enantiomer of the magnesium salt or omeprazole having a degree of crystallinity of under 67% by weight and having a residual organic solvent content of less than 7% by weight.

2. The process of claim 1 wherein the enantiomer is S-omeprazole.

3. The process of claim 1 wherein the enantiomer is R-omeprazole.

4. The process of claim 1, 2 or 3 wherein the lower alcohol is methanol.

5. The process of claim 1, 2 or 3 wherein the flash-evaporation is done by spray-drying the solution.

6. Magnesium S-omeprazole having a residual organic solvent content of less than 7% by weight and having degree of crystallinity of under 67%.

7. Magnesium S-omeprazole of claim 6 having a residual organic solvent content of less than 5% by weight.

8. Magnesian S-omeprazole of claim 6 having a residual organic solvent content of less than 2% by weight.

9. Magnesium S-omeprazole of claim 6 having a residual organic solvent content of less than 1% by weight.

10. Magnesium S-omeprazole of claim 6, having a degree of crystallinity of under 60%.

11. Magnesium S-omeprazole of claim 6, having a degree of crystallinity of wider 50%.

12. Magnesium S-omeprazole of claim 6, having a degree of crystallinity of wider 25%.

13. A solid pharmaceutical composition for oral administration comprising magnesium S-omeprazole of claim 6 in combination with a pharmaceutically acceptable excipient.

14. The composition of claim 13 in the form of a tablet.

15. The composition of claim 14 wherein the tablet is enteric coated.

16. Magnesium R-omeprazole having a residual organic solvent content of less than 7% by weight and having a degree of crystallinity of under 67%.

17. Magnesium R-omeprazole of claim 16 having a residual organic solvent content of less than 5% by weight.

18. Magnesium R-omeprazole of claim 16 having a residual organic solvent content of less than 2% by weight.

19. Magnesium R-omeprazole of claim 16 having a residual organic solvent content of less than 1% by weight.

20. Magnesium R-omeprazole of claim 16 having a degree of crystallinity of under 60%.

21. Magnesium R-omeprazole of claim 16 having a degree of crystallinity of under 50%.

22. Magnesian R-omeprazole of claim 16 having a degree of crystallinity of under 25%.

23. A solid pharmaceutical composition for oral administration comprising magnesium R-omeprazole of claim 16 in combination with a pharmaceutically acceptable excipient.

24. The composition of claim 23 in the form of a tablet.

25. The composition of claim 24 wherein the tablet is enteric coated.

26. The composition of claim 6, wherein magnesium S-omeprazole is in substantially amorphous form.

27. The composition of claim 16, wherein magnesium R-omeprazole is in substantially amorphous form.

28. The composition of claim 15 or 25 further comprising a separating layer between said enteric coating and said tablet.

* * * * *